United States Patent
Pretz et al.

(10) Patent No.: US 8,669,406 B2
(45) Date of Patent: Mar. 11, 2014

(54) PROCESS FOR THE PREPARATION OF HYDROGENATED HYDROCARBON COMPOUNDS

(75) Inventors: Matthew T. Pretz, Lake Jackson, TX (US); Susan B. Domke, Rosharon, TX (US); William M. Castor, Lake Jackson, TX (US); Simon J. Hamper, Lake Jackson, TX (US)

(73) Assignee: Dow Global Technologies LLC

( * ) Notice: Subject to any disclaimer, the term of this patent is extended or adjusted under 35 U.S.C. 154(b) by 0 days.

(21) Appl. No.: 13/348,236

(22) Filed: Jan. 11, 2012

(65) Prior Publication Data

US 2012/0123177 A1    May 17, 2012

Related U.S. Application Data

(63) Continuation of application No. 12/940,286, filed on Nov. 5, 2010, now abandoned, which is a continuation of application No. 10/586,024, filed as application No. PCT/US2005/003772 on Feb. 4, 2005, now abandoned.

(60) Provisional application No. 60/543,006, filed on Feb. 9, 2004.

(51) Int. Cl.
C07C 5/32        (2006.01)
C07C 5/327       (2006.01)

(52) U.S. Cl.
USPC ........... 585/440; 585/441; 585/443; 585/444; 585/661; 585/624

(58) Field of Classification Search
None
See application file for complete search history.

(56) References Cited

U.S. PATENT DOCUMENTS

| | | | | |
|---|---|---|---|---|
| 5,254,788 A * | 10/1993 | Gartside et al. | ............... | 585/659 |
| 6,045,688 A * | 4/2000 | Ruottu et al. | ............... | 208/113 |
| 2002/0198428 A1* | 12/2002 | Iezzi et al. | ............... | 585/654 |
| 2005/0177016 A1* | 8/2005 | Sanfilippo et al. | ............ | 585/444 |
| 2011/0230698 A1 | 9/2011 | Towler et al. | | |

* cited by examiner

*Primary Examiner* — Tam M Nguyen

(57) ABSTRACT

A process for the dehydrogenation of a paraffinic hydrocarbon compound, such as an alkane or alkylaromatic hydrocarbon compound to produce an unsaturated hydrocarbon compound, such as an olefin or vinyl aromatic compound or mixture thereof, in which a dehydrogenation catalyst contacts gaseous reactant hydrocarbons in a reactor at dehydrogenation conditions.

7 Claims, 5 Drawing Sheets

PROCESS FOR THE PREPARATION OF HYDROGENATED HYDROCARBON COMPOUNDS

This application is a continuation application of U.S. patent application Ser. No. 12/940,286, filed Nov. 5, 2010, which is a continuation of U.S. patent application Ser. No. 10/586,024, filed Jul. 14, 2006, which is a 371 of PCT/US2005/003772 filed Feb. 4, 2005, which claims the benefit of U.S. Provisional Application No. 60/543,006 filed 9 Feb. 2004.

Parties to the Joint Development Agreement were Snamprogetti S.p.A and The Dow Chemical Company.

BACKGROUND OF THE INVENTION

1) Field of the Invention

This invention generally relates to the field of hydrocarbon conversion and particularly to the dehydrogenation of paraffinic hydrocarbons to olefinic hydrocarbons, and/or lower alkylaromatic hydrocarbons to vinyl aromatic hydrocarbons. In several preferred embodiments, the invention relates to the dehydrogenation of lower alkanes, for example ethane, isopropane, propane and butanes to their corresponding olefins, for example ethylene, propylene and butylenes; and/or to the dehydrogenation of lower alkylaromatic hydrocarbon compounds, for example ethylbenzene, propylbenzene and methylethylbenzene to their corresponding vinyl aromatic (that is "alkenylaromatic") hydrocarbon compounds, for example styrene, cumene and alpha-methyl styrene, respectively. The invention further includes an integrated process for making olefinic and vinyl aromatic hydrocarbons including alkylation and dehydrogenation steps.

2) Description of Related Art

U.S. Pat. No. 6,031,143 and its corresponding EP 0 905 112 describe an integrated process for producing styrene by feeding benzene and recycled ethylene to an alkylation reactor to produce ethylbenzene, mixing the alkylation effluent with ethane and feeding the mixture to a dehydrogenation reactor containing a catalyst capable of contemporaneously dehydrogenating ethane and ethylbenzene. The resulting product is separated to produce a stream of styrene and ethylene, with ethylene being recycled to the alkylation reactor. The dehydrogenation reactor is preferably a fluidized bed reactor connected to a fluidized bed regenerator from which the catalyst is circulated between the regenerator and the dehydrogenation reactor in countercurrent flow. That is, catalyst is introduced to the dehydrogenation reactor from the top and slowly descends to the bottom in countercurrent with the gas phase reactants which are rising through the reactor. During this descent, the catalyst is deactivated. The deactivated catalyst is removed from the bottom of the dehydrogenation reactor and transported to the top of the regenerator where it descends to the bottom in countercurrent flow with hot air which is rising. During this descent, the carbonaceous residue present on the catalyst is burnt and the regenerated catalyst is collected at the bottom of the regenerator where it is subsequently circulated back to the top of the dehydrogenation reactor.

WO 02/096844 describes an improvement to this process where the dehydrogenation catalyst is transported from the regenerator to the dehydrogenation reactor by way of a lower alkyl hydrocarbon carrier, for example ethane. During transport, a portion of the carrier is dehydrogenated, (for example ethane converted to ethylene), and the catalyst is cooled.

EP 1 255 719 (and corresponding co-pending US patent publication no. US 2003/0028059, both filed by the assignee of the present application) describes a similar integrated process of preparing styrene using benzene and ethane as raw materials. However, the process includes additional separation and recycling steps that are designed to improve efficiency. For example, the dehydrogenated effluent exiting the dehydrogenation reactor is separated into its aromatic and non-aromatic constituents. The non-aromatic constituents, namely ethane, ethylene and hydrogen are recycled to an alkylation reactor were they are combined with benzene. The aromatic constituents are further separated, for example styrene is recovered and ethylbenzene is recycled to the dehydrogenation reactor. The alkylation effluent is separated into its constituents with hydrogen being removed, and ethane and ethylbenzene being directed to the dehydrogenation reactor. The dehydrogenation reactor may have a variety of conventional designs including fixed, fluidized, and transport bed.

The described dehydrogenation processes are effective at integrating the production of styrene and ethylene using ethane and benzene as the starting materials. Thus, these processes effectively de-coupled the production of styrene from the presence or proximity of a light hydrocarbon steam cracker as a source for ethylene. However, the dehydrogenation processes described employ relatively long contact times between the hydrocarbons and catalyst while at reaction temperature, resulting in thermal cracking, undesired side reactions and the formation of tars and other heavy products.

WO 02/096844 introduces the concept of a split "riser-type" dehydrogenation reactor operating in concurrent or "equicurrent" mode wherein catalyst is carried upwards pneumatically through the dehydrogenation reactor by the gas phase reactants. The space velocity (GHSV) for such a reactor is greater than $500^{h-1}$. The catalyst is introduced into the reactor with an alkyl hydrocarbon such as ethane whereas the alkylaromatic compound, for example ethylbenzene, is introduced at a suitable height along the riser after much of the alkyl hydrocarbon has be dehydrogenated and the temperature of the catalyst has been reduced. While no specific examples or operating conditions are provided, the use of such a riser reactor presumably leads to reduced contact times between reactants and catalyst while in the reactor.

Dehydrogenation temperatures and residence times are typically optimized to balance the reaction kinetics of both catalytic and gas-phase (thermal) reactions. The catalytic reaction produces a high selectivity to the desired products while the gas phase reaction produces many undesired products and impurities. That is, while the catalytic reaction kinetics to the desired products increases exponentially with temperature so does the gas phase reaction kinetics; therefore, the proper residence time and reaction temperature profile must be selected to drive both the catalytic reaction to the desired conversion while not allowing the non-selective gas phase reactions to overwhelm the total product selectivity. It would be useful to provide an apparatus and process which minimizes the time period in which reactants and catalyst are in contact with one another while at reaction temperature. This is particularly the case when utilizing highly reactive catalyst which can quickly deactivate.

While not directed toward a "dehydrogenation process" as described in the aforementioned references, WO 03/050065 describes an integrated process for making styrene where benzene and "recycled" ethylene are combined in an alkylation unit with the resulting product stream of ethylbenzene being combined with ethane. Unlike the previously described references, this process utilizes an oxidative dehydrogenation (oxodehydrogenation) reaction. That is, the product stream from the alkylation unit is combined with ethane and oxygen and then contemporaneously oxidatively dehydrogenated to provided ethylene and styrene. The resulting ethylene is recycled to the alkylation unit. The oxodehydrogenation reactor is described as a fluid-bed reactor operating at a temperature range of from 300 to 550° C., a pressure range from 1 to 30 bar, a gas hourly space velocity of 2000 to 6000$^{h-1}$, with a residence time of the catalyst in the fluid-bed zone of from 1 to 60 seconds.

BRIEF SUMMARY OF THE INVENTION

The above described deficiencies of prior art can be overcome by the subject invention which comprises contacting a gaseous stream of hydrocarbon with a dehydrogenation catalyst at reaction temperature for relatively short "contact times." In a preferred embodiment, lower alkanes, for example ethane, propane and butanes are dehydrogenated to their corresponding olefins, for example ethylene, propylene and butylenes; and/or lower alkylaromatic hydrocarbon compounds, for example ethylbenzene, propylbenzene and methylethylbenzene are dehydrogenated to their corresponding vinyl aromatic hydrocarbon compounds, for example styrene, cumene and alpha-methyl styrene, respectively.

In another embodiment, the aforementioned dehydrogenation process is combined with an alkylation step, as part of an integrated process. Many additional embodiments are also described.

DETAILED DESCRIPTION OF THE INVENTION

Figure 1:
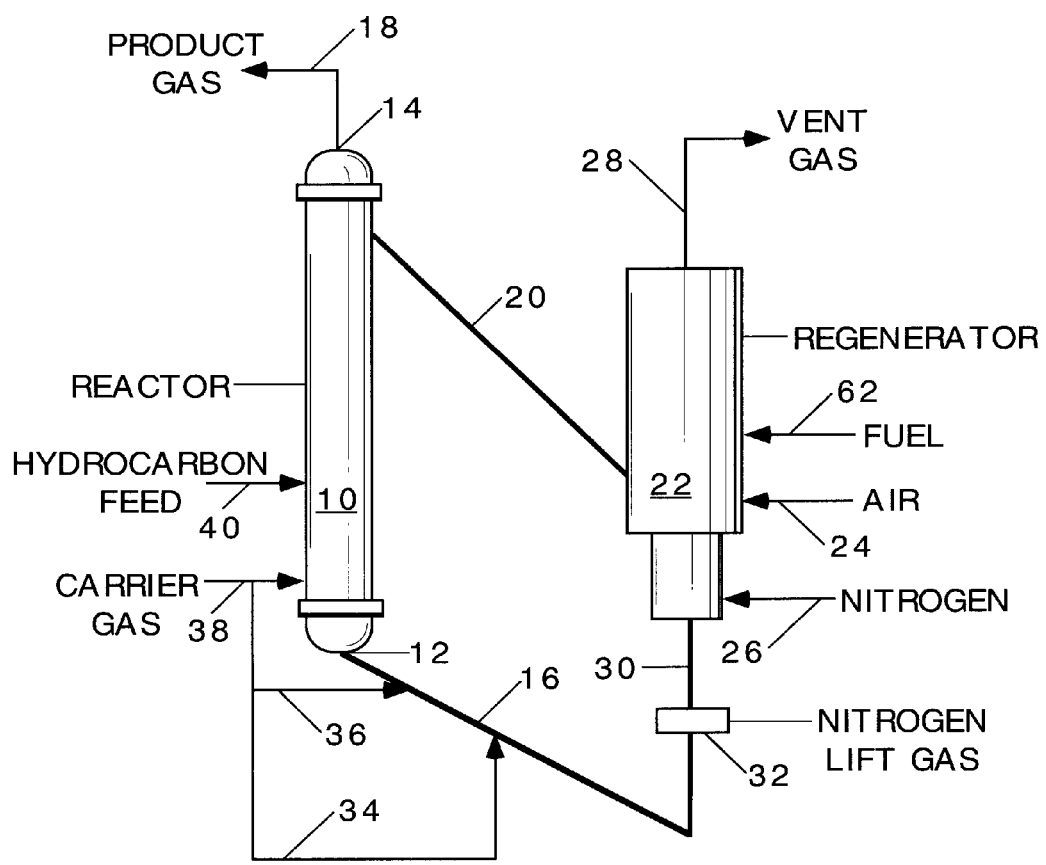
FIG. 1 shows a schematic block flow diagram of an embodiment of the present invention in which a riser reactor is employed in a single hydrocarbon feed point which may be used for: 1) paraffinic hydrocarbon (for example ethane) feed only, 2) alkylaromatic hydrocarbon (for example ethylbenzene) feed only, or 3) mixed feed (for example ethane and ethylbenzene), including catalyst regeneration.

The present invention is directed toward the dehydrogenation of at least one and preferably both of: 1) a paraffinic hydrocarbon compounds, preferably a lower alkane having from 2 to 6 carbon atoms but more preferably less than 5 carbon atoms, for example ethane, propane, isopropane and butanes, to the corresponding olefin, namely, ethylene, propylene, and butylenes, respectively, and 2) an alkylaromatic hydrocarbon compound, preferably a lower alkylaromatic hydrocarbon compound, such as for example, ethylbenzene, propylbenzene, isopropyl benzene, and methyl ethylbenzene, to the corresponding vinyl aromatic hydrocarbon compound, (that is "alkenylaromatic"), namely, styrene, cumene or alpha-methyl styrene. Several embodiments of the present invention are described including both the simultaneous and separate dehydrogenation of lower alkanes and alkylaromatics. The invention is useful to prepare styrene and ethylene from ethylbenzene and ethane, respectively. Likewise, cumene and propylene can be prepared from propylbenzene and propane, respectively.

The dehydrogenation reaction in the present invention is conducted under a relatively short contact times in order to prevent undesirable side reactions and product degradation. The term "average contact time" or "contact time" as used herein is intended to refer to the time in which the molar average of gaseous hydrocarbon molecules are in contact with catalyst while at reaction temperature, regardless of whether the reactants are converted to desired products. The term "reaction temperature" is intended to mean a temperature at which a significant amount of chemical reaction occurs, regardless of whether such reactions are the desired dehydrogenation of reactants to their corresponding olefin and vinyl aromatic products. Said another way, the reaction temperature is the temperature at which the hydrocarbons are no longer stable. The term "significant amount" in intended to mean a detectable amount having in an economic impact on the process. In most embodiments of the invention, the reaction temperature is greater than about 500 and preferably 550° C. The average contact time needs to be sufficiently long to dehydrogenate acceptable amounts of hydrocarbon reactants but not so long as to result in unacceptable amounts of by-products. While the required contact time is related to the specific reactants, catalysts and reaction temperatures, in preferred embodiments of the invention the contact time within the dehydrogenation reactor is less than 60 seconds, preferably from about 0.5 to about 10 seconds, more preferably from about 1 to about 8 seconds, and still more preferably from about 1 to about 4 seconds.

Due to the active nature of the preferred catalyst, the average residence time of the catalyst within the dehydrogenation reactor is preferably less than about 60 seconds, preferably from about 0.5 to about 40 seconds, more preferably about 1.0 to about 12.0 seconds, and still more preferably from about 1.0 to about 10 seconds.

At such short catalyst residence times and average contact times in the dehydrogenation reactor, the temperature of the reaction mixture, which may be supplied in major part by the hot fresh or regenerated catalyst, is preferably from about 500 to about 800° C. With respect to lower alkanes, the reaction mixture is preferably from about 600 to about 750° C., and with respect to alkylaromatics from about 550 to 700° C. but more preferably from about 570 to about 660° C. In general, the highest temperature in the reactor will be found at its lower end and as reaction proceeds and the catalyst and reaction mixture ascends, the temperature will decrease toward the upper end of the reactor.

The applicable operating pressure of the dehydrogenation reactor is quite broad, that is from about 3.7 to about 64.7 psia. The pressure at which the reaction proceeds is typically from about 14.7 to about 64.7 psia, and preferably from about 14.7 to about 44.7 psia. However, in several preferred embodiments of the invention, the operating pressure of the dehydrogenation reactor may be below atmospheric, that is from about 3.7 to 14.7 psia, more preferably about 6.0 to about 14.7 psia.

The gas hourly space velocity (GHSV) for the present process has been found to range from about 1,000 to about 150,000 normal cubic meters/hr of hydrocarbon feed per cubic meter of catalyst at bulk density. The superficial gas velocity of about 5 to about 80 ft/sec, preferably about 15 to about 70 ft/sec. The catalyst flux is preferably about 10 to about 120 lbs/ft$^2$-sec with a catalyst to feed ratio of about 5 to about 100 on a weight to weight basis. The catalyst is preferably pneumatically moved through the reaction system by a carrier fluid, which is preferably either an inert diluent fluid or one of the reactants in gaseous form. Alternatively, the catalyst may be transported through the reactor under sub atmospheric pressure without diluent. Examples of inert diluent carrier gases are nitrogen, volatile hydrocarbons for example methane, and other carriers which do not interfere with the reaction, steam, carbon dioxide, argon and the like. The paraffinic hydrocarbon compounds useful as reactants in the process of the present invention are also preferred carrier fluids and, most preferred are ethane, propane, and butane. Steam is preferably not used in the present invention. The amount of carrier gas required is only that amount necessary to maintain the catalyst particles in fluidized state and transport the catalyst from the regenerator to the reactor. Preferably, the amount of carrier gas employed can range from about 0 to about 0.2 kg gas/kg catalyst. Injection points for carrier gas, especially reactant feed material carrier gas can be made at multiple points along the fresh or regenerated catalyst transfer line connecting the regenerator with the lower end of the riser reactor. The carrier gas will exit the reactor with the product gas or through the vent stream of the regenerator. In the case where the carrier gas is also a reactant, a considerable portion of the carrier gas may be reacted and leave with the product gas stream from the reactor.

The short contact time required by the present invention can be accomplished by way of a number of known reactor designs including fast fluidized, riser and downer reactors. Riser reactors are well known and commonly employed in conversion of certain petroleum fractions into gasoline in fluidized bed catalytic cracking (FCC) processes. See for example U.S. Pat. No. 3,888,762 which describes a short-time dilute-phase riser reactor designed for contact times of about 10 seconds, and which further includes catalyst regeneration and recycle configurations—incorporated herein by reference. See also: US Publication No. 2004/0082824; WO 2001/85872 and WO 2004/029178. In an FCC process, a solid particulate catalyst, usually an acidic clay, silica-alumina or synthetic or natural zeolite type of catalyst, is introduced with a carrier fluid to the lower end of a long, cylindrical or tubular reaction vessel together with a petroleum fraction at elevated temperature and moderate pressure. The cracking process occurs in the petroleum as the liquid petroleum is vaporized by the hot catalyst and both rise in the reactor cylinder. At the top of the riser reactor, the catalyst and hydrocarbon product are separated and the gasoline product stream exits via a vent pipe for separation and further processing into gasoline and heating oil fractions. The catalyst settles in an annular space between the outside wall of the riser tube and an inner wall of the reactor housing through which a stripper gas contacts the catalyst, at a rate which does not prevent settling of the catalyst, and strips off additional petroleum product from the catalyst surface. The catalyst is then sent to a regenerator/reactivator in which the catalyst is contacted with a regeneration fluid, usually an oxygen-containing gas for combustion of any remaining hydrocarbons, heavy residuals or tars, and the regenerated catalyst is sent back to the lower end of the riser reactor to contact additional petroleum for cracking. Spent catalyst may also be directly recycled to the lower end of the reactor without regeneration.

In a similar manner, in a preferred embodiment of the present invention the alkylaromatic hydrocarbon compound and/or the paraffinic hydrocarbon compound are introduced to the lower end of a reactor and contacted by the hot fresh or regenerated catalyst which is pneumatically moved by a carrier gas. As the hydrocarbon compound(s) rise in the cylindrical reactor with the catalyst, the dehydrogenation reaction takes place and at the top or upper end of the riser, the vinyl aromatic hydrocarbon compound and/or lower olefin is separated from the catalyst. The riser reactor can be constructed from conventional materials used in FCC or petrochemical processing and is conveniently a steel vessel using an alloy sufficient for containing the hydrocarbon materials of the reaction, considering the temperature, pressure and flow rates employed and may be refractory lined. The dimensions of the riser reactor are dependent on the process design of a processing facility, including the proposed capacity or throughput, gas hourly space velocity (GHSV), temperature, pressure, catalyst efficiency and unit ratios of feed converted to products at a desired selectivity.

The separation of gaseous hydrocarbon and catalyst is conveniently accomplished by means of a centrifugal impingement separator, such as a cyclone separator, but the separation can by done by any conventional means for solid-gas separations, including filtration and liquid suspension. It is important to minimize the average contact time between the catalyst and hydrocarbon once they exit the dehydrogenation reactor. This is preferably accomplished by at least one of two means; physical separation of catalyst from hydrocarbon, and cooling the catalyst and/or hydrocarbon to a temperature below the reaction temperature of hydrocarbon present. The average contact time of the catalyst and hydrocarbon at reaction temperature in the separation device is typically less than 60 seconds, preferably less than about 10 seconds, and more preferably less than about 5 seconds, and still more preferably less than about 3 seconds. The separation device may be a conventional solid-gas impingement separator, such as cyclone separators commonly used in FCC applications. Preferred cyclone separators include two staged or "coupled" designs including both positive and negative pressure designs. Further examples are provided in U.S. Pat. Nos. 4,502,947; 4,985,136 and 5,248,411. Once separated, the catalyst is either recycled to the dehydrogenation reactor or transferred to a regenerator.

In addition to separating the catalyst and hydrocarbon, the separation device may include a heat exchanger and/or quenching unit for delivering a fluid to cool the catalyst and/or hydrocarbons to a temperature below the reaction temperature. Such fluid may be delivered via a conventional quenching design including pressurized nozzles for delivering quenching fluid, for example liquid styrene, water, and the like. Such quenching technology is available from Stone & Webster and BP Amoco.

The average contact time between the catalysts and hydrocarbons while at reaction temperature through the entire dehydrogenation reactor and separation device is preferably less than 60 seconds, more preferably less than about 20 seconds, and still more preferably less than about 10 seconds, and event more preferably less than about 7 seconds.

Once separated, the gaseous hydrocarbon is further separated, that is aromatics and non-aromatics, etc., which may be part of an integrated process as described in U.S. Pat. No. 6,031,143; WO 02/096844; and US 2003/0028059. The spent catalyst may then optionally be sent to a stripper, and then either to a regenerator or recycle loop, after which the catalyst is returned to the dehydrogenation reactor. During regeneration the catalyst is contacted with a regeneration fluid, usually an oxygen-containing gas and optionally a fuel source such as methane or natural gas where remaining hydrocarbons, coke, heavy residues, tar, etc. are removed from the catalyst, and the resulting regenerated catalyst is cycled back to the dehydrogenation reactor. A portion of the spent catalyst may be cycled back to the dehydrogenation reactor without regeneration via a recycle loop. Recycled spent catalyst may be combined with regenerated catalyst as a means of controlling temperature and catalyst activity within the dehydrogenation reactor. The combination of recycled and regenerated catalyst may be optimized based upon feedback from the output of the dehydrogenation reactor. An example of a means for controlling this combination is described in WO 03/083014, incorporated herein by reference. Examples of both regeneration and recycle configurations are provided in U.S. Pat. No. 3,888,762 and US 2003/0196933, which are also incorporated herein by reference.

Preferred catalysts for use in the present invention are very active and are capable of dehydrogenating paraffin and alkylaromatic hydrocarbons in less than a few seconds at ideal reaction temperatures. Preferred catalyst include solid particulate type which are capable of fluidization and, preferably, a those which exhibit Geldart A properties, as known in the industry. Gallium-based catalyst described in U.S. Pat. No. 6,031,143 and WO 2002/096844 and are particularly preferred in the present process and are incorporated herein by reference. One class of preferred catalyst for the dehydrogenation reaction is based on gallium and platinum supported on alumina in the delta or theta phase, or in a mixture of delta plus theta phases, or theta plus alpha phases, or delta plus theta plus alpha phases, modified with silica, and having a surface area preferably less than about 100 $m^2/g$, as determined by the BET method known to those skilled in the field. More preferably, the catalyst comprises:

i) from 0.1 to 34 percent by weight, preferably 0.2 to 3.8 percent by weight of gallium oxide ($Ga_2O_3$);

ii) from 1 to 200 parts per million (ppm), preferably 100 to 150 ppm by weight of platinum;

iii) from 0.05 to 5 percent be weight, preferably 0.1 to 1 percent by weight of an alkaline and/or earth-alkaline such as potassium;

iv) from 0.08 to 3 percent by weight silica;

v) the balance to 100 percent being alumina.

Similar gallium-based catalyst are described in WO 2003/053567 which further includes manganese; and US 2004/02242945 which further includes zinc, and EP-B1-0,637,578. The description of the catalyst from these documents is expressly incorporated herein by reference.

Another suitable catalyst for the dehydrogenation reaction is based on chromium and comprises:

i) from 6 to 30 percent, preferably, from 13 to 25 percent, by weight of chromium oxide ($Cr_2O_3$);

ii) from 0.1 to 3.5 percent, most preferably, from 0.2 to 2.8 percent, by weight stannous oxide (SnO);

iii) from 0.4 to 3 percent, most preferably, from 0.5 to 2.5 percent, by weight of an alkaline oxide, for example, potassium oxide;

iv) from 0.08 to 3 percent by weight silica;

v) the balance to 100 percent being alumina in the delta or theta phase, or a mixture of delta plus theta phases, or theta plus alpha phases, or delta plus theta plus alpha phases.

The catalysts mentioned hereinabove can be used as such or diluted with an inert material, for example, alpha-alumina, possibly modified with oxides of alkaline metals and/or silica, at a concentration of the inert product of between 0 and 50 percent by weight. Details on the preparation of the aforementioned catalysts and their more preferred species can be found in U.S. Pat. No. 6,031,143 and EP-B1-0,637,578. Typically, the process of preparing the aforementioned dehydrogenation catalysts comprises dispersing precursors of the catalytic metals, for example, solutions of soluble salts of the catalytic metals onto the carrier consisting of alumina or silica. An example of dispersion can comprise impregnation of the carrier with one or more solutions containing the precursors of gallium and platinum, or with one or more solutions of the precursors of chromium and tin, followed by drying and calcination. An alternative method comprises ion adsorption followed by the separation of the liquid portion of the adsorption solution, drying, and activation of the resultant solid. As another alternative, the carrier can be treated with volatile species of the desired metals. In the case of added alkaline or alkaline earth metals, the addition procedure comprises co-impregnation of the alkaline or alkaline earth metal with the primary catalytic metals (that is, Ga and Pt, or Cr and Sn), or alternatively, addition of the alkali or alkaline earth metal to the carrier prior to dispersion of the primary catalytic metals, and thereafter, possible calcination of the solid.

Other suitable dehydrogenation catalysts, based on iron oxide, are disclosed in EP 1 216 219. These catalyst comprise:

(i) from 1 to 60 percent, preferably from 1 to 20 percent, by weight iron oxide;

(ii) from 0.1 to 20 percent, preferably from 0.5 to 10 percent, by weight of at least one alkaline or alkaline earth metal oxide, more preferably, potassium oxide;

(iii) from 0 to 15 percent, preferably, from 0.1 to 7 percent, by weight of at least one rare earth oxide, preferably, selected from the group consisting of cerium oxide, lanthanum oxide, praseodymium oxide, and mixtures thereof;

(iv) the complement to 100 percent being a carrier consisting of a microspheroidal alumina with a diameter selected from those in delta or theta phase, or in a mixture of theta plus alpha phases, or in a mixture of delta plus theta plus alpha phases, modified preferably with from 0.08 to 5.0 weight percent of silica.

The carrier in the preferred iron oxide catalyst more preferably has an average particle diameter and particle density such that the final product can be classified as Group-A according to Geldart (Gas Fluidization Technology, D. Geldart, John Wiley & Sons) and a surface area of less than about 150 $m^2/g$, as measured by the BET method known to those skilled in the art. The process of preparing the iron oxide catalyst is well known and fully described in EP 1 216 219

Another applicable dehydrogenation catalyst consists of a mordenite zeolite, optionally, promoted with a metal selected from gallium, zinc, the platinum group metals, or a combination thereof, as described in U.S. Pat. No. 5,430,211 and incorporated herein by reference. The mordenite is preferably acid extracted and thereafter impregnated or ion-exchanged with one or more metals selected from gallium, zinc, and the platinum group metals, more preferably, gallium. In this catalyst, the total metal loading typically ranges from 0.1 to 20 weight percent, based on the total weight of the catalyst.

As mentioned, the preferred catalyst for use with the present invention are very active and are capable of completing the dehydrogenation reaction in a relatively short reaction time, for example in matter of seconds. Consequently, if the catalyst is allowed to remain in contact with the hydrocarbon mixture at reaction temperature for a longer period than necessary to complete the dehydrogenation reaction, undesirable by-products are formed from unreacted starting materials and/or the desired products are degraded by a continued exposure to the catalyst at process conditions. The use of short contact times between the hydrocarbon and catalyst while at reaction temperature in the dehydrogenation reactor results in an unexpectedly beneficial conversion, selectivity and decrease in the amounts of by-products formed. This unexpected effect is magnified by the use of short contact times between the hydrocarbon products and catalyst while at reaction temperature in the separation device. Further, the use of a reactor with relatively short contact or residence time decreases the amount of catalyst required for the process. A lower catalyst inventory provides operating and capital advantages compared with prior art processes.

BRIEF DESCRIPTION OF THE SEVERAL VIEWS OF THE DRAWINGS

Several preferred embodiments of the invention are illustrated in the attached figures. Turning to FIG. 1, a tubular cylindrical riser reactor 10 having a lower end 12 and an upper end 14 is connected at its lower end 12 to a fresh or regenerated catalyst transfer line 16 and at its upper end 14 to a product gas exit line 18. Spent or deactivated catalyst is removed from the product gas at upper end 14 by a separation device (not shown) which can be a conventional solid-gas impingement separator, such as a cyclone separator as previously described, and the catalyst is sent via spent catalyst transfer line 20 to regenerator 22 which is a reaction vessel in which combustion air is blown into the regenerator 22 by means of air line 24. Supplemental fuel may be added via fuel line 62 to provide the heat of reaction and necessary sensible heat, including the heat of vaporization in the case of liquid feed in the riser reactor 10. The combustion products from the oxidation of hydrocarbon on the catalyst are removed from the regenerator 22 by means of vent gas line 28. Prior to being sent for disposal or additional heat recovery, the vent gas may be filtered for removal of catalyst fines and dust by conventional equipment which is not shown. As a result of the combustion and hydrocarbon removal the catalyst is regenerated and heated to a temperature sufficient to dehydrogenate the hydrocarbon feed materials and is removed from the regenerator 22 by means of regenerated catalyst exit line 30. Fluidization is maintained by injection of a diluent or carrier gas, for example nitrogen, by means of nitrogen injection lines 26 and 32, and carrier gas injection lines 34, 36, and 38, so that catalyst is introduced to the lower end 12 of riser reactor 10 where it contacts ethane which is introduced via hydrocarbon feed line 40.

While FIG. 1 has been described with reference to the dehydrogenation of ethane, it will be appreciated that the present invention, along with the embodiment of FIG. 1 is also applicable for the dehydrogenation of other hydrocarbons, including lower alkanes such as propane and butane, and lower alkylaromatics, such as ethylbenzene, propylbenzene and methylethylbenzene.

In operation, the embodiment shown in FIG. 1 proceeds by feeding regenerated catalyst at a temperature of from about 600 to about 800° C. from the regenerator 22 by means of regenerated catalyst exit line 30 into fresh or regenerated catalyst transfer line 16 with the catalyst being maintained in a fluid state of a Geldart A solid particulate material by means of fluidizing inert gas, such as nitrogen, fed through nitrogen injection lines 26 and 32, and carrier gas, which may be inert (again, such as nitrogen) or a reactant gas, such as a paraffinic hydrocarbon, such as for example, a lower alkane, preferably ethane, propane, or a butane, via carrier gas injection lines 34, 36, and 38. This catalyst and carrier gas mixture is introduced to the lower end 12 of riser reactor 10 and contacts a hydrocarbon feed in liquid or gaseous form, preferably the latter, introduced by means of hydrocarbon feed line 40. The catalyst and hydrocarbon feed, for example, a lower alkane, such as ethane, propane or a butane, or an alkylaromatic hydrocarbon compound, or a mixture of both lower alkane and an alkylaromatic hydrocarbon compound, contacts the catalyst and rises in the riser reactor 10 with the catalyst, feed (which by this time has been transformed into a gas) and the carrier gas. As the catalyst-feed-carrier gas mixture rises in the reactor, the dehydrogenation reaction occurs and the feed is converted into a lower olefin and/or a vinyl aromatic compound, depending on the feed material. As the reaction mixture containing gas and catalyst arrives at the upper end 14 of riser reactor 10, the catalyst and gaseous reaction mixture are separated by a solid-gas separation device, such as an impingement separation device which may preferably be a cyclone gas-solid separator, which is conventional and not shown, but which is well known to those of skill in the art of the FCC industry. The separated product gas is sent to recovery and purification and the catalyst is sent for regeneration and re-heating by means of spent or deactivated catalyst transfer line 20. As the spent or deactivated catalyst is introduced into the regenerator 22, it contacts heated combustion air which is introduced by air line 24 and supplemental fuel introduced by fuel line 62, such that the hydrocarbon materials remaining on the surface of the catalyst are burned off and exit the regenerator via vent gas line 28. The combustion process also serves a second purpose and that is to heat the catalyst so that the catalyst can function as a heat transfer agent or medium in the riser reactor 10. As used in this embodiment, the hydrocarbon feed 40 can be a paraffinic hydrocarbon such as a lower alkane, an alkylaromatic hydrocarbon compound, or a mixture of the two.

Figure 2:
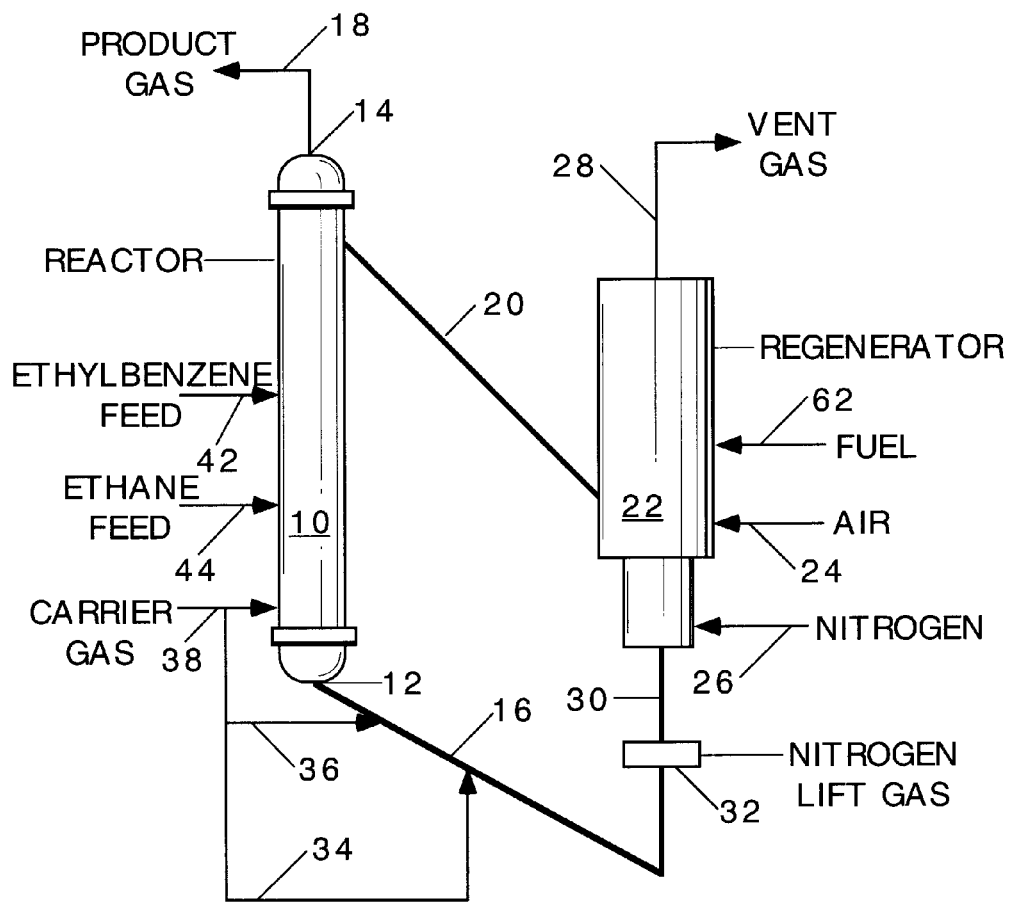
FIG. 2 shows a schematic block flow diagram of another embodiment of the present invention in which a riser reactor is employed with a multiple feed point configuration, that is a split ethylbenzene and ethane feed configuration, including catalyst regeneration.

FIG. 2 illustrates another preferred, non-limiting embodiment which is a variant on the process of the present invention using a similar riser reactor 10 configuration as described with respect to FIG. 1. In this embodiment the paraffinic hydrocarbon (for example ethane) is fed to the riser reactor 10 at or adjacent the lower end 12 by means of ethane feed line 44 and the lower alkylaromatic hydrocarbon compound (for example ethylbenzene), is fed at a higher point in the riser reactor 10, for example at ethylbenzene feed line 42. Thus, the type of reaction illustrated by the process of FIG. 2 is a "split feed" riser reactor process which produces styrene and by-products, such as ethylene which can be returned to an alkylation step to react with additional benzene to produce more ethylbenzene as part of an integrated process.

Figure 3:
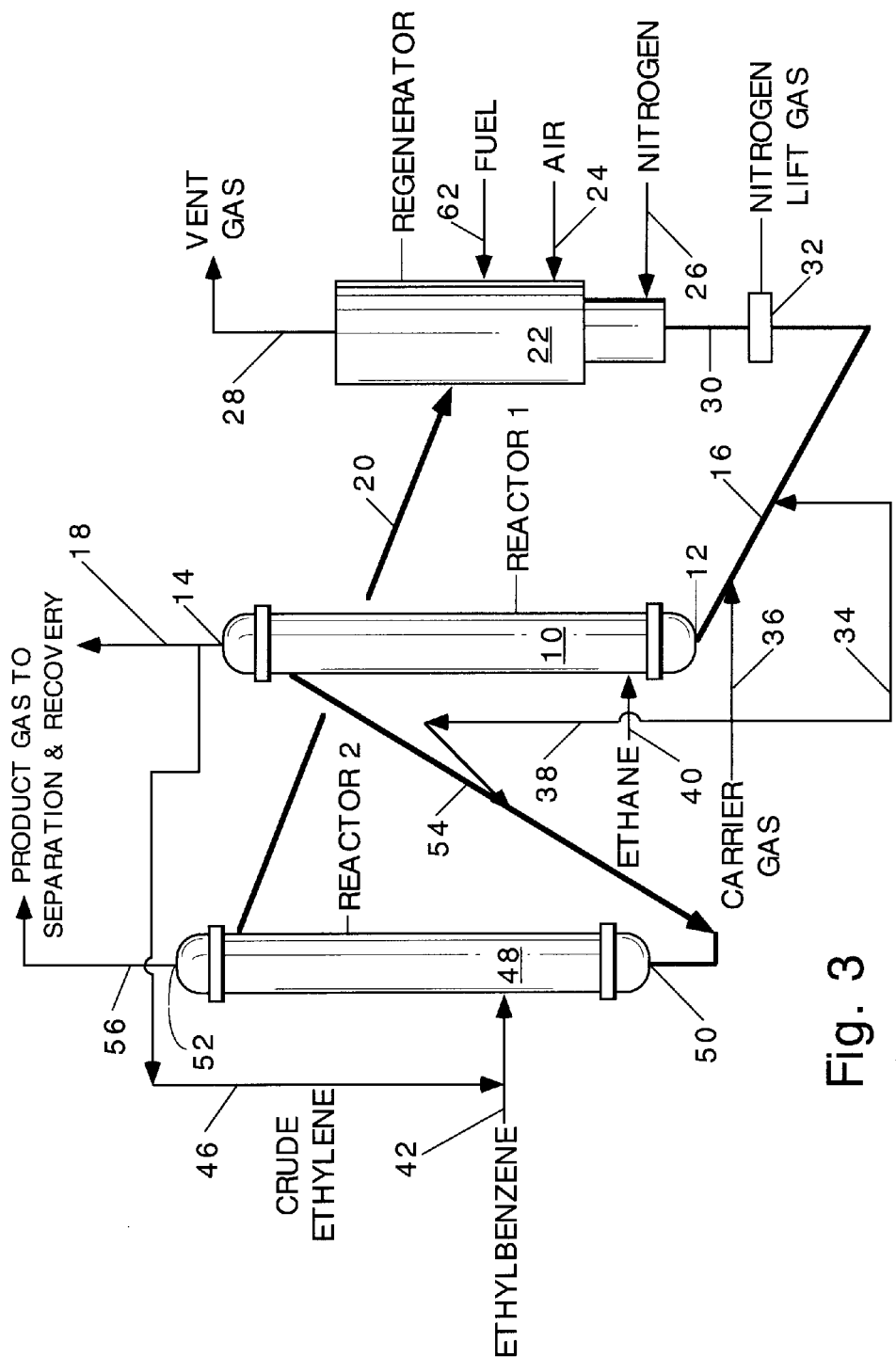
FIG. 3 shows a schematic block flow diagram of another embodiment of the present invention including multiple riser reactors with a catalyst regeneration in a series configuration.

FIG. 3 illustrates yet another preferred, non-limiting embodiment of the invention. In this embodiment, a "dual riser" reactor configuration is illustrated in which the riser reactors 10 and 48 are connected in series. As shown in FIG. 3, riser reactor 10 has lower end 12 and upper end 14. Connected to lower end 12 is fresh or regenerated catalyst line 16 and the catalyst is maintained in fluidized state by injection of carrier gas via lines 34 and 36. Hydrocarbon feed material, such as ethane, is introduced to the lower end 12 of riser reactor 10 by means of hydrocarbon feed line 40. At this stage of the process, the configuration is much like that of FIG. 1; however, the product gas from riser reactor 10 in FIG. 3 is fed to a separation and recovery section (not shown) by means of product gas exit line 18 from which a side product gas line 46 leads to an alkylaromatic hydrocarbon compound feed line, such as ethylbenzene feed line 42. Alternatively, both side product gas line 46, which carries primarily the lower olefin produced in riser reactor 10 in addition to by-products and carrier gas, can be fed separately into a second riser reactor, such as at 48, having a lower end 50 and an upper end 52. Also entering the lower end 50 of second riser reactor 48 is a partially deactivated catalyst line 54 which leads from the upper end 14 of riser reactor 10 to the lower end 50 of second riser reactor 48. Carrier gas line 38 can be used to introduce fluidizing carrier gas into partially deactivated catalyst line 54 at one or multiple points along partially deactivated catalyst line 54. As the ethylene and ethylbenzene rise in second riser reactor 48 with the catalyst and carrier gas, the catalyst is at a lower temperature than when initially introduced to the lower end 12 of riser reactor 10. The relatively lower temperature than in riser reactor 10 permits satisfactory reaction rates for the alkylaromatic hydrocarbon compound and prevents over reaction to undesired by-products, thus decreasing the yield, conversion and selectivity of the dehydrogenation reaction. The upper end 52 of second riser reactor 48 is connected to second product gas exit line 56 and can lead the vinyl aromatic hydrocarbon compound, such as crude styrene monomer contained in the product gases, into the product gas separation and recovery section, which is conventional and not further described or identified herein. Prior to exit from second riser reactor 48, the reaction mixture must be separated from the deactivated catalyst and this is done in a solid-gas separation device, such as a cyclone separator, not shown. The separated and deactivated catalyst is fed back to the regenerator 22 by means of spent or deactivated catalyst transfer line 20 which in this embodiment leads from the upper end 52 of second riser reactor 48 to the regenerator 22 where the catalyst is regenerated, as previously described. In operation, the process is much like that described in relation to the process illustrated in FIGS. 1 and 2, except that the product gas from the upper end 14 of riser reactor 10 is split and a portion is introduced into the lower end 50 of second riser reactor 48. Ethylbenzene is also introduced into the lower end 50 of second riser reactor 48 along with the partially deactivated catalyst via partially deactivated catalyst line 54 and the dehydrogenation of the ethylbenzene proceeds at somewhat milder conditions in second riser reactor 48 than in riser reactor 10. At the upper end 52 of second riser reactor 48, the product gases are separated from the catalyst in a solid gas separator device, such as a cyclone separator (which is conventional and not shown) and the product gases exit via second product gas exit line 56 and the catalyst is sent back to regenerator 22 for regeneration and reheating via spent or deactivated catalyst transfer line 20.

Figure 4:
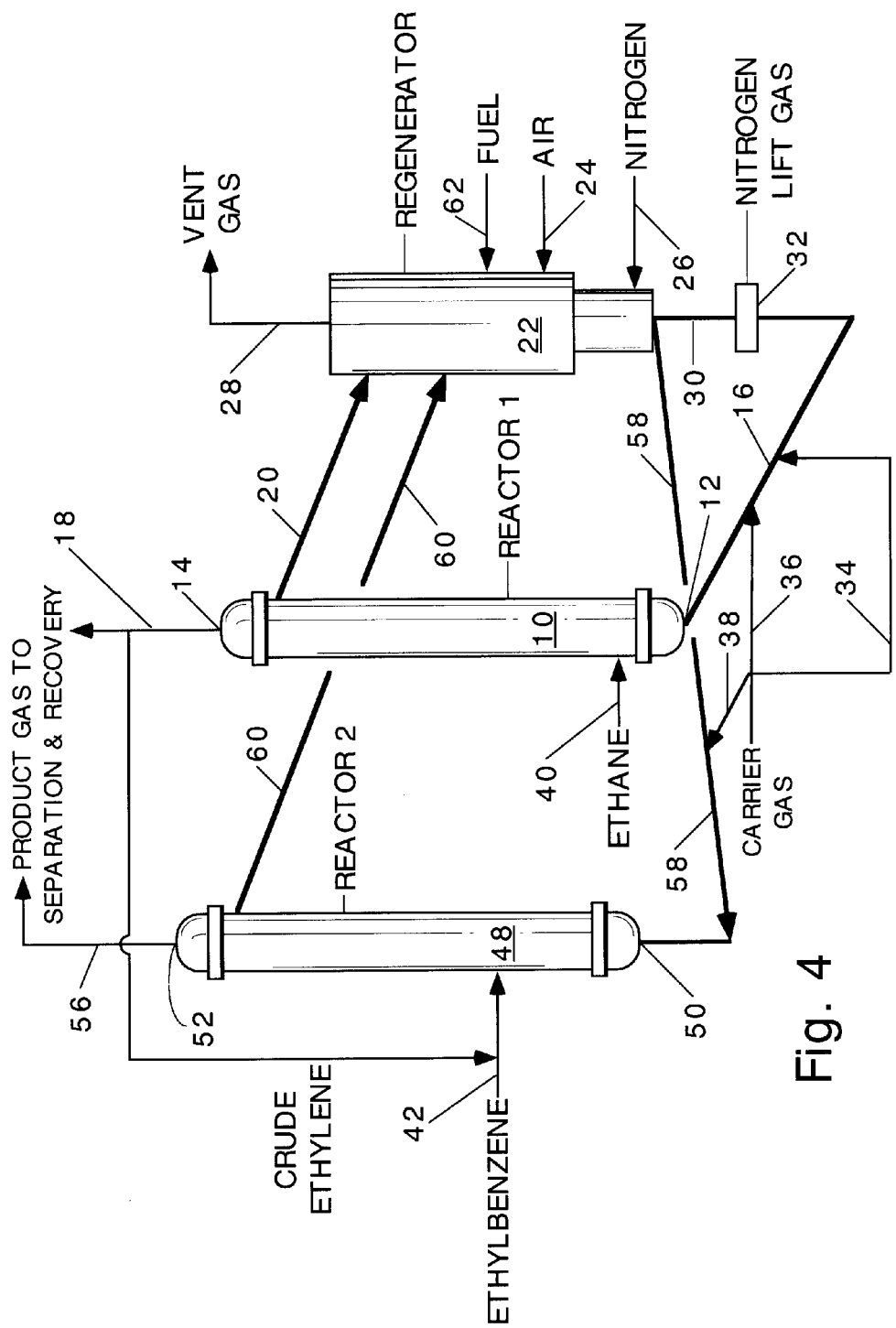
FIG. 4 shows a schematic block flow diagram of another embodiment of the present invention including multiple riser reactors with catalyst regeneration in a parallel configuration.

In a still further preferred embodiment of this invention shown in FIG. 4, the reactor/regenerator configuration is similar to that of FIG. 3, except that the second riser reactor 48 has its own catalyst feed and removal transfer lines, namely second fresh or regenerated catalyst transfer line 58 and second spent or deactivated catalyst transfer line 60 which feed active catalyst to second riser reactor 48 and remove catalyst from it and send the deactivated or spent catalyst back to regenerator 22. While shown as utilizing a common regenerator 22, it will be appreciated that each reactor may include a separate regenerator.

In operation and as shown in FIG. 4, the catalyst from regenerator 22 is led by regenerated catalyst exit line 30 to either riser reactor 10 or second riser reactor 48 via fresh or regenerated catalyst transfer line 16 or second fresh or regenerated catalyst transfer line 58, respectively. The feed to riser reactor 10 is ethane via hydrocarbon feed line 40 and to second riser reactor 48 is ethylbenzene via ethylbenzene feed line 42. On contact with the catalyst in the riser reactors, the ethane and ethylbenzene are converted into ethylene and styrene monomer, respectively, and the crude gaseous products are separated from the catalyst in gas-solid separators, such as cyclone separators (not shown) and sent to product gas separation and recovery operations (not shown) to produce ethylene for recycle to make additional ethylbenzene and styrene monomer, respectively. In a similar manner and using propane or butane instead of ethane feed, the process of this invention would dehydrogenate the feed to propylene or butylenes, respectively; or using isopropyl benzene or methyl ethyl benzene as feed material, the process of this invention would dehydrogenate the feed to cumene or alpha-methyl styrene, respectively.

Figure 5:
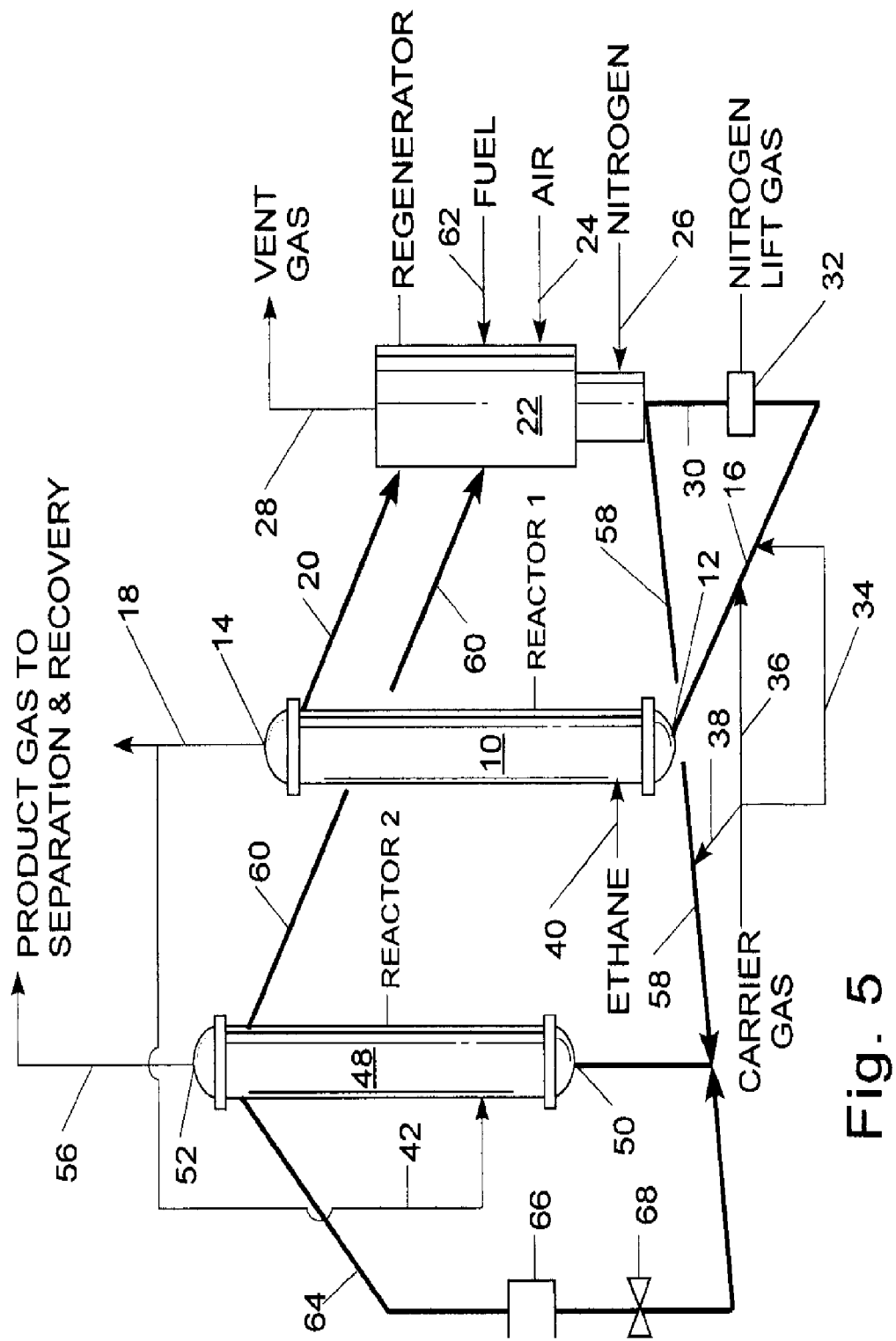
FIG. 5 shows a schematic block follow diagram of another embodiment of the present invention similar to FIG. 4, but further including a catalyst recycle configuration.

FIG. 5 illustrates yet another embodiment of the invention similar to that shown in FIG. 4 but with the addition of a catalyst recycle loop comprising a catalyst transfer line 64, carrier gas injector line 66 and flow valve 68. Spent catalyst is removed from the product gas at the upper end 52 of the dehydrogenation reactor 48 via a separation device (not shown) and is recycled back to the bottom end 50 of the reactor 48 via catalyst transfer line 64. Fluidization of the spent catalyst is maintained by the injection of a carrier gas, for example nitrogen by means of injection line in module 66. In addition to providing a carrier gas, an oxygen-containing gas may be introduced in order to partially reactivate the catalyst, in which case module 66 would include a chamber for reaction and removal of hydrocarbon residue. Flow of catalyst through the recycle loop is controlled by one or more valves, for example 68 which may be controlled remotely according to predetermined performance criteria including reactor 48 temperature, catalyst activity, etc. Recycled catalyst may be combined with regenerated catalyst prior to introduction in the bottom of reactor 48, or may be introduced via separate entry points (not shown).

Additional configurations of the reactor(s), regenerator and recycle loop can be envisioned by one skilled in the art. For example, one skilled in the art will appreciate that multiple reactors could be arranged to feed into a common separation device with shared or separate catalyst regenerators and various recycle loops. The present invention is desired to be limited only by the lawful scope of the appended claims The present invention does not preferably include oxidative dehydrogenation, that is oxodehydrogentation. In fact, oxygenates can poison some types of catalyst; however, oxygen may be used to regenerate or reactivate catalyst during the regeneration process. Moreover the present invention preferably does not utilize steam as is typically used in convention styrene production process.

Another preferred embodiment of the invention utilizes the previously described dehydrogenation process as part of an integrated process for making olefins and vinyl aromatics. More specifically, the previously described dehydrogenation, (along with regeneration and/or recycle processes) can be used to replace the dehydrogenation schemes described in U.S. Pat. No. 6,031,143; WO 02/096844; and co-pending US 2003/0028059. In such an integrated process, a paraffinic hydrocarbon such as a lower alkane, for example ethane, and benzene are the primary raw materials. Ethylene, preferably "recycled" and benzene are feed to a conventional alkylation reactor as is well known in the art and as described in the references mentioned above, hereby incorporated by reference. Alkylation of benzene with ethylene in typically conducted in the presence of aluminum chloride or zeolites catalyst. Variations include the use of dilute ethylene and a catalytic distillation approach where liquid phase alkylation and product separation take place simultaneously. Specific examples include the "EBOne Process" available from ABB Lummus/UOP, "EB Max Process" available from ExxonMobil/Badger and similar alkylation technology available from CDTECH, a partnership between ABB Lummus Global Inc. and Chemical Research and Licensing.

The alkylation affluent is recovered and optionally subject to separation, that is separation of aromatics from non-aromatics, removal of hydrogen, etc. Alkylaromatic, for example ethylbenzene, and paraffinic hydrocarbon, for example ethane, are then dehydrogenation as previously described. The gaseous products of dehydrogenation are recovered and separated, for example aromatics from non-aromatics, with vinyl aromatics, for example styrene being recovered, olefins, for example ethylene (and possibly paraffinic hydrocarbons, for example ethane) being recycled to the alkylation reactor, and alkylaromatics being recycled to the dehydrogenation reactor.

The invention claimed is:

1. A process for dehydrogenating a hydrocarbon selected from at least one of:
   i) paraffinic hydrocarbons selected from ethane, propane, and butane; and
   ii) alkylaromatic hydrocarbons selected from ethylbenzene, propylbenzene and methylethylbenzene; comprising
   contacting a gaseous stream containing at least one of the hydrocarbons with a dehydrogenation catalyst comprising gallium and platinum and carried by an alumina or alumina silica support, at reaction temperature and in concurrent rising flow, at a catalyst to hydrocarbon ratio of 5 to 100 on a weight to weight basis, to a dehydrogenation reactor wherein the average contact time between the hydrocarbon and catalyst within the dehydrogenation reactor is from about 1 to about 4 seconds; and the temperature and pressure in the dehydrogenation reactor is from about 570 to about 750° C., and from about 6.0 to about 44.7 psia; and
   transferring the hydrocarbon and catalyst from the dehydrogenation reactor to a two stage solid-gas impingement separator comprising a cyclone separation device wherein the average contact time between the hydrocarbon and catalyst while at reaction temperature in the separation device is less than about 5 seconds and the total average contact time between the hydrocarbon, catalyst and resulting hydrocarbons while at reaction temperature is less than about 10 seconds; and
   transferring catalyst from the separation device to a regenerator where the catalyst is contacted with an oxygen-containing regeneration fluid and supplemental fuel.

2. The process of claim 1 wherein the catalyst comprises an alkali or alkaline earth metal selected from at least one of: sodium, lithium, potassium, rubidium, magnesium, calcium, strontium and barium.

3. A process of claim 1 wherein the catalyst has an average residence time within the dehydrogenation reactor from about 0.5 to about 40 seconds.

4. A process of claim 1 wherein the dehydrogenation reactor is a riser reactor.

5. A process of claim 1 wherein the dehydrogenation reactor is a fast fluidized reactor.

6. A process of claim 1 wherein catalyst from the separation device is transferred to one of: a catalyst regenerator wherein the catalyst is regenerated and returned to the dehydrogenation reactor, and a recycle loop wherein catalyst is recycled from the separation device back to the dehydrogenation reactor.

7. A process of claim 6 wherein the catalyst from the recycle loop and regenerator are combined and introduced into the dehydrogenation reactor.

* * * * *